United States Patent
Wang et al.

(10) Patent No.: US 11,158,180 B2
(45) Date of Patent: Oct. 26, 2021

(54) EMERGENCY CARE DEVICE

(71) Applicant: Wistron Corp., New Taipei (TW)

(72) Inventors: Jia-Syun Wang, New Taipei (TW); Hsin-Shui Chen, New Taipei (TW)

(73) Assignee: WISTRON CORP., New Taipei (TW)

( * ) Notice: Subject to any disclaimer, the term of this patent is extended or adjusted under 35 U.S.C. 154(b) by 0 days.

(21) Appl. No.: 16/749,557

(22) Filed: Jan. 22, 2020

(65) Prior Publication Data
US 2021/0090421 A1    Mar. 25, 2021

(30) Foreign Application Priority Data
Sep. 23, 2019   (TW) ................. 108212496

(51) Int. Cl.
*G08B 21/02* (2006.01)
*G08B 21/04* (2006.01)
(Continued)

(52) U.S. Cl.
CPC ....... *G08B 21/0492* (2013.01); *G08B 3/1008* (2013.01); *G08B 5/222* (2013.01);
(Continued)

(58) Field of Classification Search
CPC ...... H05B 47/19; H05B 47/105; H05B 47/16; H05B 45/37; H05B 45/10; H05B 45/20; H05B 45/00; H05B 47/11; H05B 45/50; Y02B 10/72; Y02B 20/42; Y02B 20/348; Y02B 20/44; Y02B 20/48; Y02B 70/3216; Y02B 70/3283; Y02B 90/2607; Y02B 20/46; H02J 9/02; H02J 7/34; H02J 9/065; H02J 7/0068; H02J 7/345; H02J 9/061; H02J 13/00006; H02J 13/00017; H02J 13/0017; H02J 50/00; H02J 50/10; H02J 50/40; H02J 7/0029; H02J 7/00306; H02J 7/00308; H02J 7/0042; H02J 7/025; H02J 7/34; H02J 9/061; Y10T 307/359; Y10T 307/344; Y10T 307/615; Y10T 307/625; F21K 9/23; F21K 9/238; F21S 9/022; F21V 23/0442; F21Y 2115/10; F21Y 2115/15; H02H 3/08; H02H 3/20; H04L 67/10; H04L 67/10; Y04S 20/221; Y04S 20/246;
(Continued)

(56) References Cited

U.S. PATENT DOCUMENTS 10,332,623 B2 *  6/2019  Edwards ................ G16H 10/60
10,446,017 B1 * 10/2019  Gershoni ........... G08B 21/0492
(Continued)

*Primary Examiner* — Daniel Previl

(57) ABSTRACT

An emergency care device is provided. The emergency care device includes a device housing, a processing unit, a temperature sensor, at least one touch sensor, and a signal transmitting unit. The processing unit is disposed in the device housing. The temperature sensor is coupled to the processing unit, wherein the temperature sensor is adapted to send a temperature sensing signal to the processing unit. The touch sensor is coupled to the processing unit, wherein the touch sensor is adapted to send a touch sensing signal to the processing unit. The signal transmitting unit is coupled to the processing unit, wherein the processing unit controls the signal transmitting unit to send an emergency signal according to the temperature sensing signal and the touch sensing signal.

9 Claims, 4 Drawing Sheets

(51) Int. Cl.
    *G08B 5/36* (2006.01)
    *G08B 7/06* (2006.01)
    *G08B 3/10* (2006.01)
    *G08B 5/22* (2006.01)

(52) U.S. Cl.
    CPC .............. *G08B 5/36* (2013.01); *G08B 7/06* (2013.01); *G08B 21/0453* (2013.01)

(58) Field of Classification Search
    CPC ........... Y04S 40/12; F41J 9/02; A61B 5/0022; A61B 5/0205; A61B 5/02438; A61B 5/14551; A61B 5/681; A61B 2560/0228; A61B 5/0261; A61B 5/04085; A61B 5/04725; A61B 5/0478; A61B 5/6803; A61B 5/7203; A61B 5/721; A61B 5/7221; A61B 5/7264; A61B 5/7275; A61B 5/7282; A61B 5/746; A61B 5/7475; A61B 2562/0219; A61B 5/0024; A61B 5/01; A61B 5/02055; A61B 5/021; A61B 5/02416; A61B 5/0245; A61B 5/0816; A61B 5/1112; A61B 5/6824; A61B 5/7455; G08B 25/08; G08B 13/1672; G08B 13/19613; G08B 25/016; G08B 21/043; G08B 21/0446; G16H 40/63; G16H 40/67; H04M 2250/22; H04M 3/42153; H04M 3/5116; H04M 11/04; H04M 1/72536; H04M 1/72569; H04M 2242/04; H04W 4/12; H04W 76/50; H04W 4/90; A61F 2002/0894; A61F 2/02; A61F 2/022; A61F 2/062; A61F 2/08; A61F 2/28; A61K 35/32; A61K 35/33; A61K 47/14; A63F 2003/0481; A63F 3/0478; A63F 2003/00018; B29C 64/112; B33Y 10/00; B33Y 80/00; C12M 21/08; C12M 33/00; G06F 1/163; G06F 1/3206; G06F 1/3209; G06F 1/3287; G06F 3/0482; G06F 3/04845; G06F 3/04883; G09G 2320/0626; G09G 3/34; G09G 3/3406; G10L 21/0208; H04R 1/028; H04R 3/04; Y02D 10/00
    USPC .............. 340/573.1, 539.13, 539.14, 539.21, 340/539.22, 539.26, 539.32, 566, 641
    See application file for complete search history.

(56) References Cited

U.S. PATENT DOCUMENTS

| | | | | |
|---|---|---|---|---|
| 2011/0260856 | A1* | 10/2011 | Rossmann | G08B 21/0266 340/539.13 |
| 2013/0184676 | A1* | 7/2013 | Kamen | G16H 20/17 604/506 |
| 2015/0168268 | A1* | 6/2015 | Fish | G01H 1/003 374/142 |
| 2016/0180222 | A1* | 6/2016 | Sierhuis | G06F 7/023 706/47 |
| 2016/0282026 | A1* | 9/2016 | Park | F24F 1/22 |
| 2017/0193172 | A1* | 7/2017 | Melle | G16H 40/20 |
| 2017/0337339 | A1* | 11/2017 | Cronin | A61B 5/0022 |
| 2018/0103859 | A1* | 4/2018 | Provenzano | A61B 5/681 |
| 2018/0116605 | A1* | 5/2018 | Newberry | A61B 5/02416 |

\* cited by examiner

EMERGENCY CARE DEVICE

CROSS REFERENCE TO RELATED APPLICATIONS

This application claims priority of Taiwan Patent Application No. 108212496, filed on Sep. 23, 2019, the entirety of which is incorporated by reference herein.

BACKGROUND OF THE INVENTION

Field of the Invention

The present invention relates to an emergency care device, and in particular to an easily activated emergency care device.

Description of the Related Art

Emergency care devices are utilized in emergency situations. They allow a user to send an emergency signal. Conventional emergency care devices include an emergency button, and the user must press the button precisely to send the emergency signal. To prevent the emergency signal from being sent by accident, conventional emergency buttons need to be pressed uniformly and vigorously for the emergency signal to be sent. However, when the user is in the state of excessive bleeding, low body-core temperature, or about to faint, the user cannot press the emergency button precisely enough, and the emergency care device therefore may not send the emergency signal.

BRIEF SUMMARY OF THE INVENTION

In one embodiment, an emergency care device is provided. The emergency care device includes a device housing, a processing unit, a temperature sensor, at least one touch sensor, and a signal transmitting unit. The processing unit is disposed in the device housing. The temperature sensor is coupled to the processing unit, wherein the temperature sensor is adapted to send a temperature sensing signal to the processing unit. The touch sensor is coupled to the processing unit, wherein the touch sensor is adapted to send a touch sensing signal to the processing unit. The signal transmitting unit is coupled to the processing unit, wherein the processing unit controls the signal transmitting unit to send an emergency signal according to the temperature sensing signal and the touch sensing signal.

In one embodiment, the device housing comprises a first surface, a second surface, a third surface and a fourth surface, the first surface is parallel to the third surface, the second surface is parallel to the fourth surface, the temperature sensor corresponds to the first surface, and the touch sensor corresponds to the second surface.

In one embodiment, the temperature sensor is disposed in the device housing and corresponds to the first surface, and the touch sensor is disposed in the device housing and corresponds to the second surface.

In one embodiment, the emergency care device further comprises a lamp warning unit, wherein the lamp warning unit is coupled to the processing unit, the processing unit controls the lamp warning unit to send a light warning signal according to the temperature sensing signal and the touch sensing signal, and the lamp warning unit is disposed on the first surface.

In one embodiment, the emergency care device further comprises a sound speaker, wherein the sound speaker is coupled to the processing unit, the processing unit controls the sound speaker to send an audio signal according to the temperature sensing signal and the touch sensing signal, and the sound speaker is disposed on the first surface.

In one embodiment, the emergency care device further comprises a sling, wherein the device housing further comprises a fifth surface and a sling connection portion, the fifth surface is perpendicular to the first surface and the second surface, the sling connection portion is formed on the first surface, and the sling is connected to the sling connection portion.

In one embodiment, when the processing unit continuously receives the touch sensing signal for a first predetermined period, the processing unit judges whether a temperature value from the temperature sensing signal is within a predetermined temperature range, and if the temperature value is within the predetermined temperature range, the processing unit controls the signal transmitting unit to send the emergency signal.

In one embodiment, when the processing unit continuously receives the touch sensing signal for the first predetermined period, the processing unit judges whether the temperature value from the temperature sensing signal is within the predetermined temperature range, and if the temperature value is outside the predetermined temperature range, and the processing unit continuously receives the touch sensing signal for a second predetermined period, the processing unit controls the signal transmitting unit to send the emergency signal.

In one embodiment, the emergency care device further comprises a positioning unit, and the processing unit enters an emergency state according to the temperature sensing signal and the touch sensing signal, and in the emergency state, the positioning unit is activated by the processing unit to provide positioning data, and the positioning data is incorporated into the emergency signal to be sent by the signal transmitting unit.

In one embodiment, the emergency care device further comprises a sound speaker, wherein the sound speaker is coupled to the processing unit, and in the emergency state, the positioning data is incorporated into the emergency signal to be sent by the signal transmitting unit, and the processing unit controls the sound speaker to send an audio signal simultaneously.

Utilizing the emergency care device of the embodiment of the invention, the user can emit an emergency signal by merely holding the device housing. Unlike with conventional devices, to emit an emergency signal, the user does not need to identify the button position, and also does not need to press the button uniformly and vigorously. Therefore, even if the user has suffered a loss of blood, low body temperature, or is about to faint, the emergency care device can still send the emergency signal. Additionally, the emergency care device of the embodiment of the invention provides multiple foolproof ways to prevent the user from sending an emergency signal by accident.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1A:
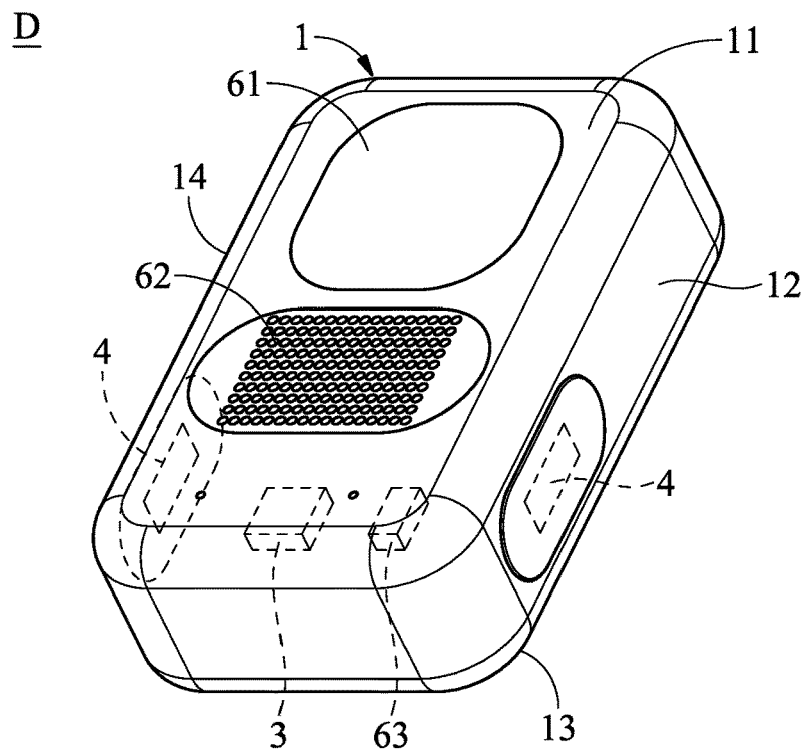
FIG. 1A is a perspective view of the emergency care device of an embodiment of the invention.
Figure 2:
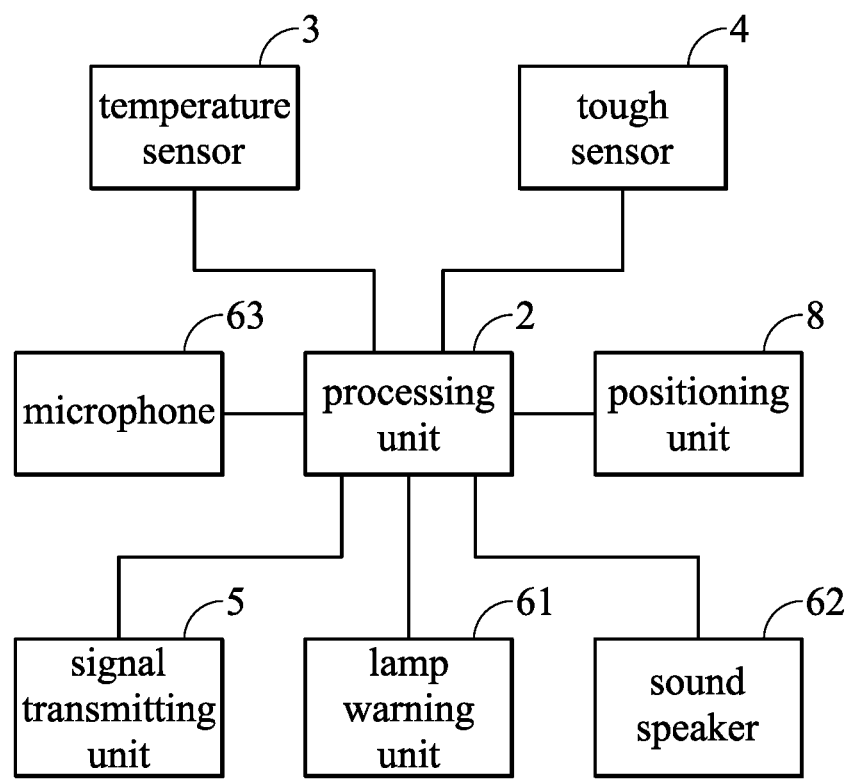
FIG. 2 is a block diagram of the emergency care device of the embodiment of the invention.

FIG. 1A is a perspective view of the emergency care device of an embodiment of the invention. FIG. 2 is a block diagram of the emergency care device of the embodiment of the invention. With reference to FIGS. 1A and 2, the emergency care device D of the embodiment of the invention includes a device housing 1, a processing unit 2, a temperature sensor 3, at least one touch sensor 4, and a signal transmitting unit 5. The processing unit 2 is disposed in the device housing 1. The temperature sensor 3 is coupled to the processing unit 2, wherein the temperature sensor 3 is adapted to send a temperature sensing signal to the processing unit 2. The touch sensor 4 is coupled to the processing unit 2, wherein the touch sensor 4 is adapted to send a touch sensing signal to the processing unit 2. The signal transmitting unit 5 is coupled to the processing unit 2, wherein the processing unit 2 controls the signal transmitting unit 5 to send an emergency signal according to the temperature sensing signal and the touch sensing signal.

With reference to FIG. 1A, in one embodiment, the device housing 1 comprises a first surface 11, a second surface 12, a third surface 13 and a fourth surface 14. The first surface 11 is parallel to the third surface 13. The second surface 12 is parallel to the fourth surface 14. The temperature sensor 3 corresponds to the first surface 11, and the touch sensor 4 corresponds to the second surface 12.

With reference to FIG. 1A, in one embodiment, the temperature sensor 3 is disposed in the device housing 1 and corresponds to the first surface 11, and the touch sensor 4 is disposed in the device housing 1 and corresponds to the second surface 12. In this embodiment, the temperature sensor 3 and the touch sensor 4 are not visible from the outside of the emergency care device D.

In one embodiment of the invention, the emergency care device D includes two touch sensors 4, which correspond to the second surface 12 and the fourth surface 14. Therefore, no matter whether the user is tightly griping the second surface 12 or the fourth surface 14, the touch sensor 4 can be activated to send the touch sensing signal. However, the disclosure is not meant to restrict the invention. For example, in another embodiment, the emergency care device D includes only one touch sensor 4, which is corresponds to the second surface 12, or one of the other surfaces of the emergency care device D.

In this embodiment of the invention, the temperature sensor 3 corresponds to the first surface 11. However, the disclosure is not meant to restrict the invention. For example, in another embodiment, the temperature sensor 3 may correspond to the third surface 13. In another embodiment, the emergency care device D may include two temperature sensors 3, and the temperature sensors 3 may correspond to the first surface 11 and the third surface 13.

With reference to FIGS. 1A and 2, in one embodiment, the emergency care device D further comprises a lamp warning unit 61. The lamp warning unit 61 is coupled to the processing unit 2. The processing unit 2 controls the lamp warning unit 61 to send a light warning signal according to the temperature sensing signal and the touch sensing signal. The lamp warning unit 61 is disposed on the first surface 11.

With reference to FIGS. 1A and 2, in one embodiment, the emergency care device D further comprises a sound speaker 62. The sound speaker 62 is coupled to the processing unit 2. The processing unit 2 controls the sound speaker 62 to send an audio signal according to the temperature sensing signal and the touch sensing signal. The sound speaker 62 is disposed on the first surface 11.

Figure 1B:
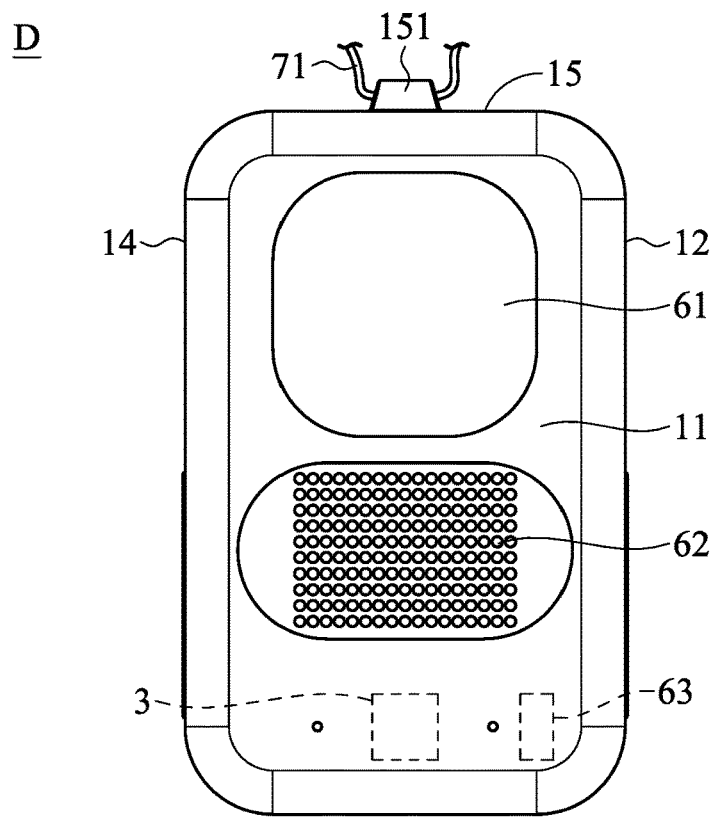
FIG. 1B is a front view of the emergency care device of the embodiment of the invention.

FIG. 1B is a front view of the emergency care device of the embodiment of the invention. In one embodiment, the emergency care device D further comprises a sling 71. The device housing 1 further comprises a fifth surface 15 and a sling connection portion 151. The fifth surface 15 is perpendicular to the first surface 11 and the second surface 12. The sling connection portion 151 is formed on the first surface 15. The sling 71 is connected to the sling connection portion 151.

In this embodiment, the temperature sensors 3 and the touch sensor 4 are relatively far from the sling connection portion 151 to increase the trigger probability in an emergency situation. However, the disclosure is not meant to restrict the invention. The locations of the temperature sensors 3 and the touch sensor 4 can be modified.

Figure 3:
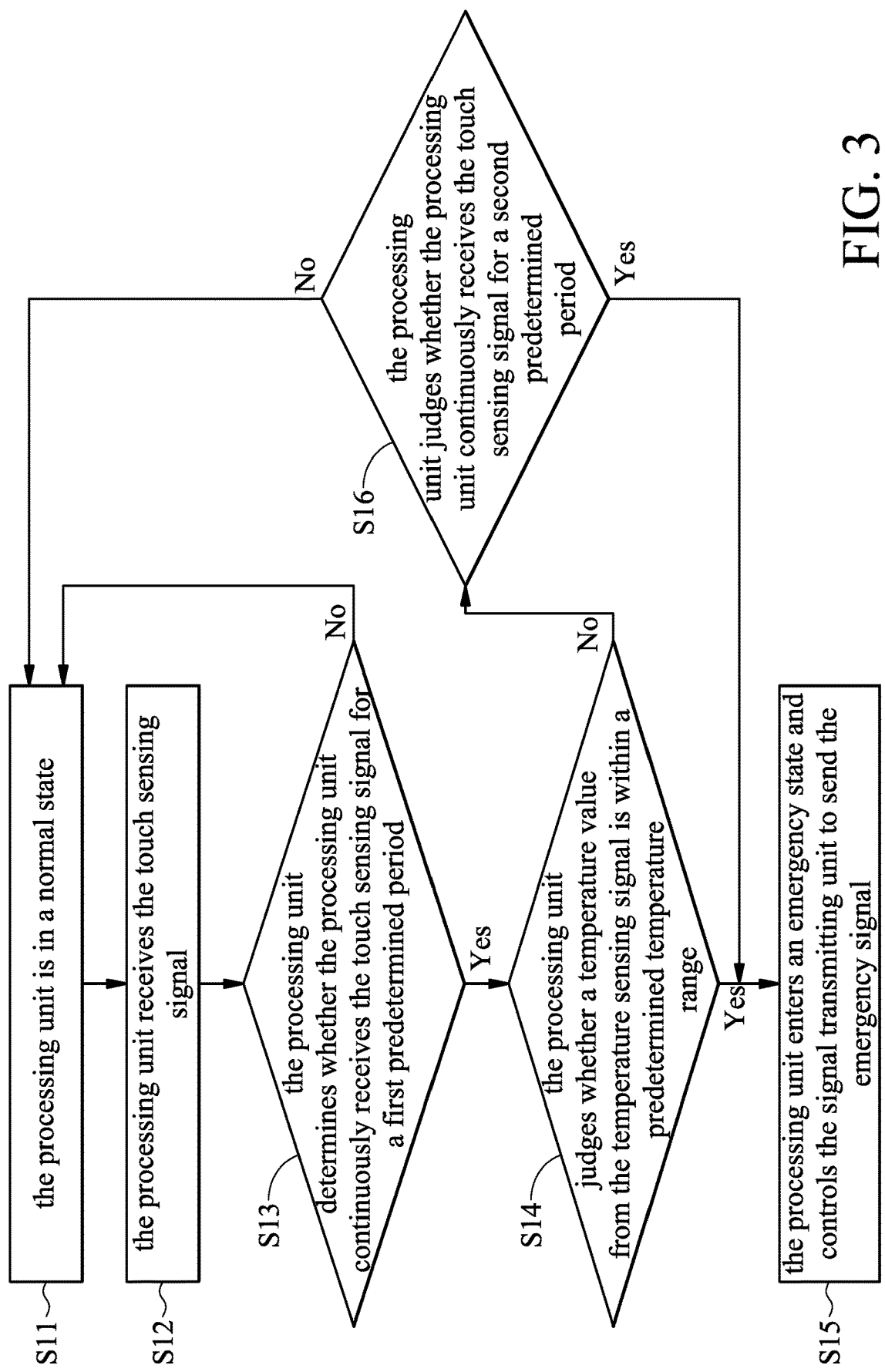
FIG. 3 is a flow chart of a determination process of the processing unit of the embodiment of the invention.

FIG. 3 is a flow chart of a determination process of the processing unit of the embodiment of the invention. With reference to FIGS. 2 and 3, the determination processes of the processing unit of the embodiment of the invention are described below. Generally, the processing unit is in a normal state (S11). Then, when the user touches the touch sensor, the processing unit receives the touch sensing signal (S12). Next, the processing unit determines whether the processing unit continuously receives the touch sensing signal for a first predetermined period (S13). If the processing unit does not continuously receive the touch sensing signal for the first predetermined period, the processing unit back to the normal state. If the processing unit continuously receives the touch sensing signal for the first predetermined period, the processing unit judges whether a temperature value from the temperature sensing signal is within a predetermined temperature range (S14). If the temperature value is within the predetermined temperature range, the processing unit enters an emergency state and controls the signal transmitting unit to send the emergency signal (S15).

With reference to FIGS. 2 and 3, in one embodiment, when the processing unit continuously receives the touch sensing signal for the first predetermined period, the processing unit judges whether the temperature value from the temperature sensing signal is within the predetermined temperature range (S14). If the temperature value is outside the predetermined temperature range, and the processing unit judges whether the processing unit continuously receives the touch sensing signal for a second predetermined period (S16). If the processing unit continuously receives the touch sensing signal for the second predetermined period, the processing unit enters the emergency state and controls the signal transmitting unit to send the emergency signal. If the processing unit does not continuously receive the touch sensing signal for the second predetermined period, the processing unit backs to the normal state.

In the embodiments above, the first predetermined period can be 5 seconds, and the second predetermined period can be 15 seconds. The predetermined temperature range can be 34°±2°. The value mentioned above can be modified.

With reference to FIG. 2, in one embodiment, the emergency care device D further comprises a positioning unit 8. The processing unit 2 enters the emergency state according to the temperature sensing signal and the touch sensing signal with the processing processes mentioned above. In the emergency state, the positioning unit 8 is activated by the processing unit 2 to provide positioning data, and the positioning data is incorporated into the emergency signal to be sent by the signal transmitting unit 5.

With reference to FIG. 2, in one embodiment, in the emergency state, the positioning data is incorporated into the emergency signal to be sent by the signal transmitting unit 5, and the processing unit 2 controls the sound speaker 62 to send an audio signal simultaneously. In another embodiment, the processing unit 2 also controls the lamp warning unit 61 to send the light warning signal.

Figure 4:
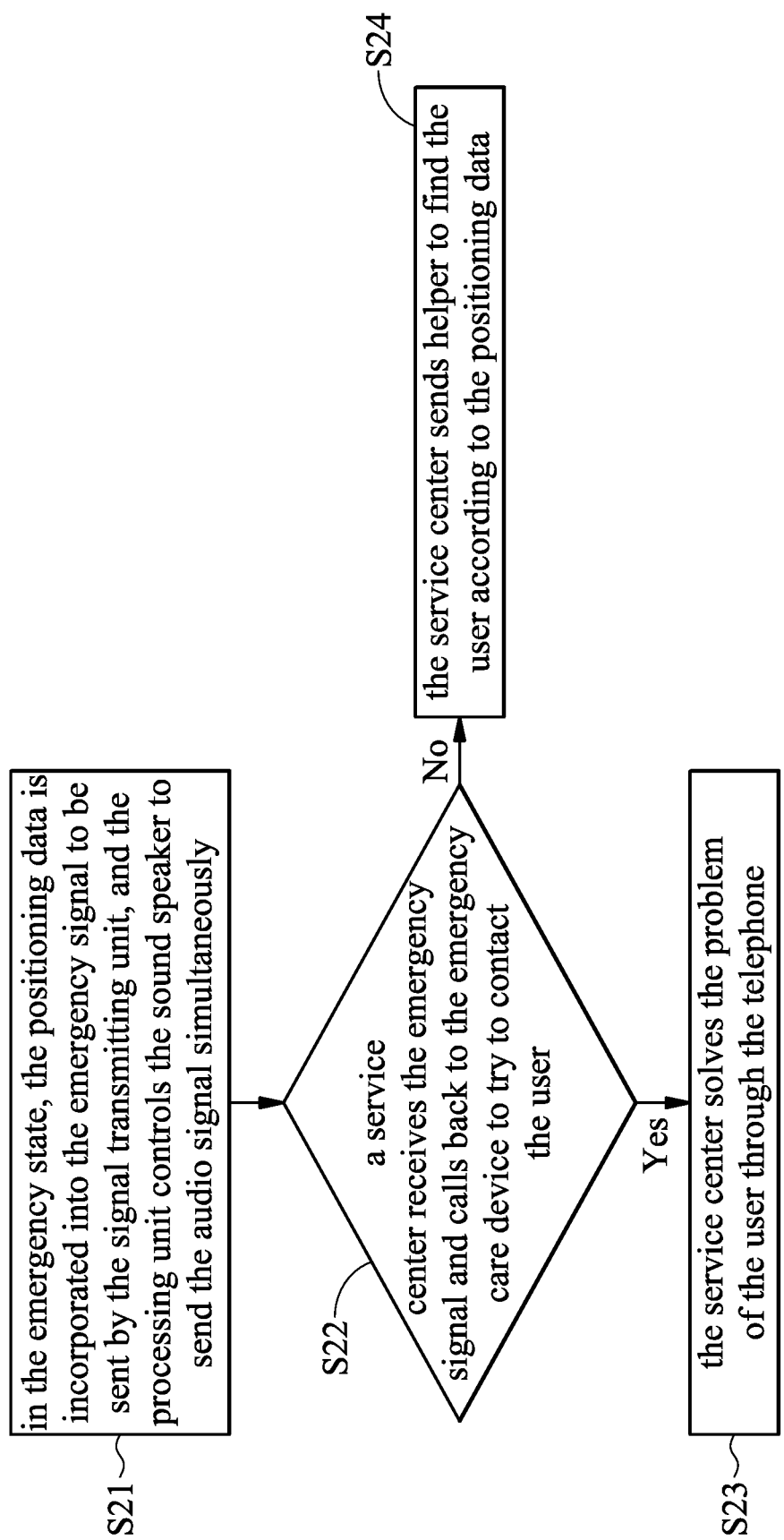
FIG. 4 is a flow chart of an emergency handling process of the embodiment of the invention.

FIG. 4 is a flow chart of an emergency handling process of the embodiment of the invention. With reference to FIG. 4, in the emergency state, the positioning data is incorporated into the emergency signal to be sent by the signal transmitting unit 5, and the processing unit 2 controls the sound speaker 62 to send the audio signal simultaneously (S21). Next, a service center receives the emergency signal and calls back to the emergency care device to try to contact the user (S22). If the service center successfully contacts the user, the service center solves the problem of the user through the telephone (S23). If the service center cannot contact the user, the service center sends helper to find the user according to the positioning data (S24).

With reference to FIGS. 1A, 1B and 2, in one embodiment, the emergency care device D further includes a microphone 63. The microphone 63 is coupled to the processing unit 2. The service center can try to contact the user via the microphone 63 and the sound speaker 62. When the service center tries to contact the user, the processing unit 2 controls the sound speaker 62 to stop sending the audio signal. The sound speaker 62 emits the voice content from the surface center.

Utilizing the emergency care device of the embodiment of the invention, the user can emit the emergency signal by merely hold the device housing. Unlike with conventional devices, to emit an emergency signal, the user does not need to identify the button position, and also does not need to press the button uniformly and vigorously. Therefore, even if the user is bleeding excessively, losing body temperature, or about to faint, the emergency care device can still send an emergency signal. Additionally, the emergency care device of the embodiment of the invention provides multiple foolproof ways to prevent the user from sending an emergency signal by accident.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term).

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An emergency care device, comprising:
    a device housing;
    a processing unit, disposed in the device housing;
    a temperature sensor, coupled to the processing unit, wherein the temperature sensor is adapted to send a temperature sensing signal to the processing unit;
    at least one touch sensor, coupled to the processing unit, wherein the touch sensor is adapted to send a touch sensing signal to the processing unit; and
    a signal transmitting unit, coupled to the processing unit, wherein the processing unit is configured such that in response to the emergency care device being held, the processing unit controls the signal transmitting unit to send an emergency signal according to the temperature sensing signal and a receiving period of the touch sensing signal,
    wherein when the processing unit continuously receives the touch sensing signal for a first predetermined period, the processing unit judges whether a temperature value from the temperature sensing signal is within a predetermined temperature range, and if the temperature value is within the predetermined temperature range, the processing unit controls the signal transmitting unit to send the emergency signal.

2. The emergency care device as claimed in claim 1, wherein the device housing comprises a first surface, a second surface, a third surface and a fourth surface, the first surface is parallel to the third surface, the second surface is parallel to the fourth surface, the temperature sensor corresponds to the first surface, and the touch sensor corresponds to the second surface.

3. The emergency care device as claimed in claim 2, wherein the temperature sensor is disposed in the device housing and corresponds to the first surface, and the touch sensor is disposed in the device housing and corresponds to the second surface.

4. The emergency care device as claimed in claim 3, further comprising a lamp warning unit, wherein the lamp warning unit is coupled to the processing unit, the processing unit controls the lamp warning unit to send a light warning signal according to the temperature sensing signal and the touch sensing signal, and the lamp warning unit is disposed on the first surface.

5. The emergency care device as claimed in claim 3, further comprising a sound speaker, wherein the sound speaker is coupled to the processing unit, the processing unit controls the sound speaker to send an audio signal according to the temperature sensing signal and the touch sensing signal, and the sound speaker is disposed on the first surface.

6. The emergency care device as claimed in claim 3, further comprising a sling, wherein the device housing further comprises a fifth surface and a sling connection portion, the fifth surface is perpendicular to the first surface and the second surface, the sling connection portion is formed on the first surface, and the sling is connected to the sling connection portion.

7. The emergency care device as claimed in claim 1, wherein when the processing unit continuously receives the touch sensing signal for the first predetermined period, the processing unit judges whether the temperature value from the temperature sensing signal is within the predetermined temperature range, and if the temperature value is outside the predetermined temperature range, and the processing unit continuously receives the touch sensing signal for a second predetermined period, the processing unit controls the signal transmitting unit to send the emergency signal.

8. The emergency care device as claimed in claim 1, further comprising a positioning unit, and the processing unit enters an emergency state according to the temperature sensing signal and the touch sensing signal, and in the emergency state, the positioning unit is activated by the processing unit to provide positioning data, and the positioning data is incorporated into the emergency signal to be sent by the signal transmitting unit.

9. The emergency care device as claimed in claim 8, further comprising a sound speaker, wherein the sound speaker is coupled to the processing unit, and in the emergency state, the positioning data is incorporated into the emergency signal to be sent by the signal transmitting unit, and the processing unit controls the sound speaker to send an audio signal simultaneously.

\* \* \* \* \*